(12) United States Patent
Saoji et al.

(10) Patent No.: US 9,307,330 B2
(45) Date of Patent: Apr. 5, 2016

(54) STAPEDIUS REFLEX MEASUREMENT SAFETY SYSTEMS AND METHODS

(75) Inventors: Aniket Saoji, Ann Arbor, MI (US); Kinuko Masaki, San Francisco, CA (US)

(73) Assignee: Advanced Bionics AG, Staefa (CH)

( * ) Notice: Subject to any disclaimer, the term of this patent is extended or adjusted under 35 U.S.C. 154(b) by 14 days.

(21) Appl. No.: 14/357,903

(22) PCT Filed: Nov. 15, 2011

(86) PCT No.: PCT/US2011/060743
§ 371 (c)(1),
(2), (4) Date: May 13, 2014

(87) PCT Pub. No.: WO2013/074086
PCT Pub. Date: May 23, 2013

(65) Prior Publication Data
US 2014/0323905 A1    Oct. 30, 2014

(30) Foreign Application Priority Data
Nov. 15, 2011 (WO) ................ PCT/US2011/060743

(51) Int. Cl.
*A61N 1/36* (2006.01)
*H04R 25/00* (2006.01)
*A61B 5/12* (2006.01)
*A61B 5/00* (2006.01)
*A61N 1/05* (2006.01)

(52) U.S. Cl.
CPC ............... *H04R 25/30* (2013.01); *A61B 5/125* (2013.01); *A61B 5/4851* (2013.01); *A61B 5/742* (2013.01); *A61B 5/7475* (2013.01); *A61N 1/36032* (2013.01); *H04R 25/606* (2013.01); *A61N 1/0541* (2013.01); *H04R 2225/67* (2013.01)

(58) Field of Classification Search
CPC . A61N 1/36032; A61N 1/0541; A61N 1/323; A61N 1/08; A61N 1/05; A61B 5/121; A61B 5/0031; A61B 5/6846; A61B 5/04001; A61B 5/053; A61B 2560/0223; A61B 5/14865; H04R 25/606; H04R 2225/67; H04R 25/30
See application file for complete search history.

(56) References Cited

U.S. PATENT DOCUMENTS

| 6,295,467 | B1 | 9/2001 | Kollmeier et al. |
| 2006/0083395 | A1 | 4/2006 | Allen et al. |
| 2007/0179565 | A1 | 8/2007 | Overstreet et al. |
| 2008/0195179 | A1* | 8/2008 | Quick .............................. 607/57 |
| 2009/0018616 | A1 | 1/2009 | Quick et al. |

OTHER PUBLICATIONS

International Search Report and Written Opinion received in International Application No. PCT/US11/060743, dated Jun. 28, 2012.

* cited by examiner

*Primary Examiner* — Deborah Malamud
(74) *Attorney, Agent, or Firm* — ALG Intellectual Property, LLC

(57) ABSTRACT

An exemplary stapedius reflex measurement safety system includes a stimulation management facility configured to direct a cochlear implant system to apply an electrical stimulus to an auditory pathway of a patient and a detection facility configured to determine that a change in acoustic immittance that occurs as the electrical stimulus is being applied by the cochlear implant system is likely representative of a rise time phase associated with an occurrence of a stapedius reflex within the patient. The stimulation management facility is further configured to direct, in response to the determination, the cochlear implant system to cease applying the electrical stimulus.

17 Claims, 8 Drawing Sheets

STAPEDIUS REFLEX MEASUREMENT SAFETY SYSTEMS AND METHODS

BACKGROUND INFORMATION

To overcome some types of hearing loss, numerous cochlear implant systems—or cochlear prostheses—have been developed. Cochlear implant systems bypass the hair cells in the cochlea by presenting electrical stimulation directly to the auditory nerve fibers by way of one or more channels formed by an array of electrodes implanted in the cochlea. Direct stimulation of the auditory nerve fibers leads to the perception of sound in the brain and at least partial restoration of hearing function.

When a cochlear implant system is initially implanted in a patient, and during follow-up tests and checkups thereafter, it is usually necessary to fit the cochlear implant system to the patient. Such "fitting" includes adjustment of the base amplitude or intensity of the various stimuli generated by the cochlear implant system from the factory settings (or default values) to values that are most effective and comfortable for the patient. For example, the intensity or amplitude and/or duration of the individual stimulation pulses provided by the cochlear implant system may be mapped to an appropriate dynamic audio range so that the appropriate "loudness" of sensed audio signals is perceived. That is, loud sounds should be sensed by the patient at a level that is perceived as loud, but not painfully loud. Soft sounds should similarly be sensed by the patient at a level that is soft, but not so soft that the sounds are not perceived at all.

Hence, fitting and adjusting the intensity of the stimuli and other parameters of a cochlear implant system to meet a particular patient's needs requires the determination of one or more most comfortable current levels ("M levels"). An M level refers to a stimulation current level applied by a cochlear implant system at which the patient is most comfortable. M levels typically vary from patient to patient and from channel to channel in a multichannel cochlear implant.

M levels are typically determined based on subjective feedback provided by cochlear implant patients. For example, a clinician may present various stimuli to a patient and then analyze subjective feedback provided by the patient as to how the stimuli were perceived. Such subjective feedback typically takes the form of either verbal (adult) or non-verbal (child) feedback. Unfortunately, relying on subjective feedback in this manner is difficult, particularly for those patients who may have never heard sound before and/or who have never heard electrically-generated "sound." For young children, the problem is exacerbated by a short attention span, as well as difficulty in understanding instructions and concepts, such as high and low pitch, softer and louder, same and different. Moreover, many patients, such as infants and those with multiple disabilities, are completely unable to provide subjective feedback.

Hence, it is often desirable to employ an objective method of determining M levels for a cochlear implant patient. One such objective method involves increasing a current level of electrical stimulation applied by a cochlear implant system to a patient until a stapedius reflex (i.e., an involuntary muscle contraction that occurs in the middle ear in response to acoustic and/or electrical stimulation) is elicited. The current level required to elicit a stapedius reflex within a patient (referred to herein as a "stapedius reflex threshold") may then be used by a clinician as a starting point for determining an M level corresponding to the patient.

Unfortunately, it is sometimes impossible to detect an occurrence of a stapedius reflex in some patients. For example, some patients may not have a functioning stapedius tendon and are therefore incapable of producing a stapedius reflex. Other patients have abnormal middle ear topologies, thereby making it impossible to detect a stapedius reflex using conventional detection techniques.

The possibility of not being able to detect an occurrence of a stapedius reflex in a patient raises various safety concerns, especially for pediatric patients incapable of providing subjective feedback. For example, if the current level of the electrical stimulation is increased very much above the M level for a particular patient, the electrical stimulation may cause pain, discomfort, and/or damage to the patient.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
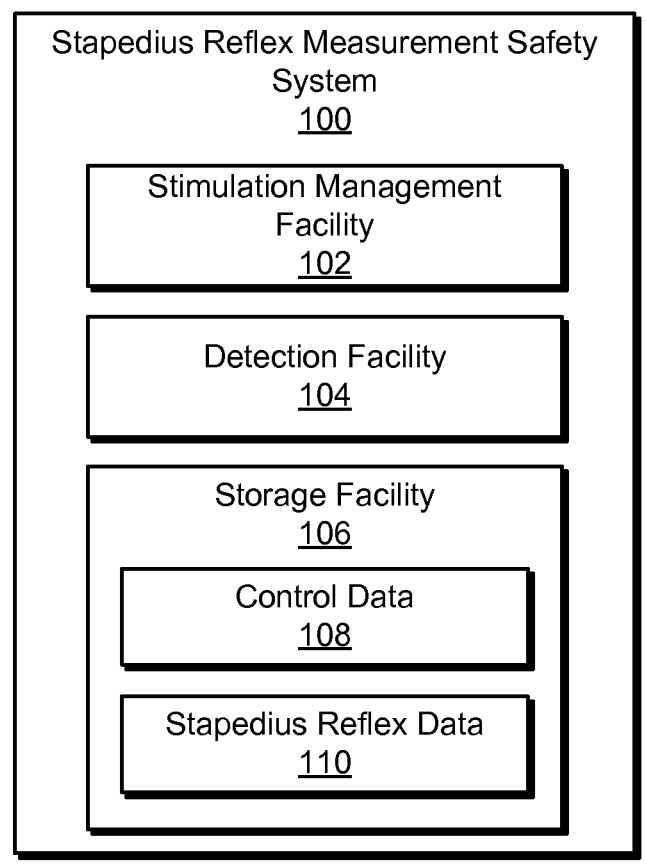
FIG. 1 illustrates an exemplary stapedius reflex measurement safety system according to principles described herein.

Stapedius reflex measurement safety systems and methods are described herein. As will be described below, the systems and methods may ensure patient safety in stapedius reflex measurement techniques that involve increasing a current level of electrical stimuli being applied to a cochlear implant patient until a stapedius reflex (also referred to as a "stapedial reflex") is detected.

For example, an exemplary stapedius reflex measurement safety system may 1) direct a cochlear implant system to apply an electrical stimulus to an auditory pathway (e.g., a location within the cochlea) of a cochlear implant patient, 2) determine that a change in acoustic immittance that occurs as the electrical stimulus is being applied by the cochlear implant system is likely representative of a rise time phase associated with an occurrence of a stapedius reflex within the patient, and 3) direct the cochlear implant system to immediately cease applying the electrical stimulus in response to the determination.

As will be described in more detail below, by directing the cochlear implant system to immediately cease applying the electrical stimulus once the stapedius reflex measurement safety system determines that a rise time phase of a stapedius reflex (i.e., an initial phase of a stapedius reflex) is likely occurring, patient exposure to the electrical stimulus may be minimized. This may minimize patient pain, discomfort, and/or damage that may result as the current level is increased in an attempt to generate an acoustic reflex.

For example, a clinician may increase the current level of electrical stimuli being applied to a cochlear implant patient starting at 100 microamps (µA) in steps of 50 µA until a middle ear analyzer detects a change in acoustic immittance that is likely representative of a stapedius reflex. At 550 µA, the middle ear analyzer still has not detected an acoustic reflex. However, at 600 µA, the middle ear analyzer detects a change in acoustic immittance that appears to be representative of an acoustic reflex. To confirm that an acoustic reflex actually occurred, the clinician may choose to increase the current level by a relatively small amount (e.g., to 625 µA). If another change in acoustic immittance occurs that appears to be representative of an acoustic reflex, the clinician may determine that an acoustic reflex did occur at 600 µA.

However, for purposes of this example, assume that the lowest current level at which the clinician could have measured an acoustic reflex is 551 µA. In this case, a current level of 600 µA may actually be above the M level of the patient and a current level of 625 µA may actually be above an uncomfortable current level ("U level") of the patient. Hence, a relatively long period of exposure by the patient to both the 600 µA and 625 µA current levels may cause pain, discomfort, and/or damage. For at least this reason, by directing the cochlear implant system to immediately cease applying the electrical stimulus once the stapedius reflex measurement safety system determines that a rise time phase of a stapedius reflex (i.e., an initial phase of a stapedius reflex) is likely occurring, patient exposure to the full loudness of the electrical stimulus (and the likelihood of harm being caused by the loudness of the electrical stimulus) may be minimized.

As another example, if the middle ear analyzer probe that is used to detect a change in immittance that occurs in response to application of electrical stimuli is relatively shallowly inserted into the patient's ear canal, the current level at which a stapedius reflex may be detected may be relatively high. For example, a stapedius reflex may not be detected until the current level is at 700 µA. Unfortunately, this current level may be higher than the M level of the patient. Once again, by directing the cochlear implant system to immediately cease applying the electrical stimulus once the stapedius reflex measurement safety system determines that a rise time phase of a stapedius reflex (i.e., an initial phase of a stapedius reflex) is likely occurring, patient exposure to the electrical stimulus may be minimized.

As an added safety measure, the stapedius reflex measurement safety system may be further configured to prevent the cochlear implant system from applying an electrical stimulus for more than a predetermined amount of time, regardless of whether the change in acoustic immittance that occurs in response to the electrical stimulus indicates that a rise time phase associated with a stapedius reflex has likely occurred. In this manner, sound saturation associated with the electrical stimulus may be prevented. As used herein, "sound saturation" refers to a state in which the electrical stimulus has been applied for a long enough duration for the cochlear implant patient to perceive the actual loudness level or sensation that corresponds to the current level of the electrical stimulus.

To illustrate, in the auditory system of most people, the loudness of a given sound saturates at about 200 milliseconds ("ms"). This means that a sound having a 60 dB loudness level, for example, has to be presented to a person for at least 200 ms to produce an actual loudness sensation of 60 dB for the person. If the 60 dB sound is presented to the person for less than 200 ms, the person perceives the sound to be softer than 60 dB. It will be recognized that the amount of time required for sound saturation to occur may vary from person to person.

The same phenomenon applies to cochlear implant patients. For example, an electrical stimulus having a current level corresponding to 60 dB must be presented to a cochlear implant patient for at least a predetermined amount of time (e.g., at least 200 ms) to produce a loudness sensation of 60 dB for the cochlear implant patient.

Hence, by preventing sound saturation from occurring within a cochlear implant patient (e.g., by preventing the cochlear implant system from applying an electrical stimulus for more than approximately 200 ms), the systems and methods described herein may allow a clinician to increase the current level of electrical stimuli applied to the patient while preventing the patient from perceiving loudness levels that are uncomfortably loud and/or that will cause damage to the ear. Because the clinician knows that sound saturation will not occur, the clinician may extend the range of current levels tested in search of a stapedius reflex for a particular patient beyond that with which the clinician may normally be comfortable.

The safety features described herein may also facilitate more efficient and effective fitting sessions in which a stapedius reflex is to be elicited. For example, a clinician may increase the step size that is used to increase the current level until a stapedius reflex is elicited without harming the patient because he or she knows that the electrical stimulation will automatically stop once a likely occurrence of a rise time phase associated with a stapedius reflex is detected or once the predetermined amount of time configured to prevent sound saturation has expired, whichever comes first. This may be especially beneficial for pediatric patients who have a difficult time remaining still during the fitting session. Other benefits and/or advantages provided by the disclosed systems and methods will be made apparent herein.

FIG. 1 illustrates an exemplary stapedius reflex measurement safety system 100 (or simply "system 100"). As shown, system 100 may include, without limitation, a stimulation management facility 102, a detection facility 104, and a storage facility 106 communicatively coupled to one another. It will be recognized that although facilities 102-106 are shown to be separate facilities in FIG. 1, any of facilities 102-106 may be combined into fewer facilities, such as into a single facility, or divided into more facilities as may serve a particular implementation.

Stimulation management facility 102 may be configured to perform one or more electrical stimulation management operations in association with an elicitation and/or detection of a stapedius reflex. For example, stimulation management facility 102 may direct a cochlear implant system to apply one or more electrical stimuli to an auditory pathway of a cochlear implant patient until a stapedius reflex is detected.

Stimulation management facility 102 may direct a cochlear implant system to apply an electrical stimulus to a patient in any suitable manner. For example, stimulation management facility 102 may direct the cochlear implant system to apply an electrical stimulus to a patient by transmitting control data representative of a current level to be used for the electrical stimulation to a sound processor included in the cochlear implant system. The sound processor may then generate one or more stimulation parameters configured to direct a cochlear implant to apply the electrical stimulus having the specified current level. In some examples, the control data transmitted by stimulation management facility 102 to the sound processor may additionally include data specifying one or more electrodes by which the electrical stimulus is to be applied.

In some examples, stimulation management facility 102 may independently generate the control data transmitted to the sound processor in response to user input. For example, a clinician may provide user input representative of a desired current level by way of a graphical user interface ("GUI") provided by stimulation management facility 102. Stimulation management facility 102 may generate the control data in accordance with the user input provided by the clinician.

Additionally or alternatively, stimulation management facility 102 may generate the control data based on an acoustic signal provided by a middle ear analyzer. A middle ear analyzer is sometimes used to objectively measure a sound level at which an acoustic stimulus elicits a stapedius reflex in a non-cochlear implant patient by applying the acoustic stimulus to the ear of the non-cochlear implant patient and recording a resulting change in acoustic immittance. In some examples, a middle ear analyzer may be adapted to a cochlear implant patient by recording a change in acoustic immittance that occurs in response to electrical stimuli provided by a cochlear implant system associated with the patient. As used herein, "acoustic immittance" may refer to an acoustic impedance, admittance, and/or combination thereof. For example, acoustic immittance may refer to a ratio of sound pressure to volume velocity within the ear canal that occurs in response to application of electrical and/or acoustic stimulation of the auditory pathway of the patient. As will be described below, a change in acoustic immittance that occurs in response to electrical stimulation may be indicative of an occurrence of a stapedius reflex.

To facilitate synchronization of the cochlear implant system with the middle ear analyzer, the middle ear analyzer may be configured to transmit an acoustic signal (i.e., an acoustic stimulus) to stimulation management facility 102, which may detect a sound level of the acoustic signal, identify a current level associated with the detected sound level, and direct the cochlear implant system to apply a stimulation pulse having the identified current level. In this manner, the cochlear implant system operates in response to and in accordance with acoustic signals provided by the middle ear analyzer. Synchronization of a middle ear analyzer and a cochlear implant system is described more fully in a related application entitled "Systems and Methods for Synchronizing an Operation of a Middle Ear Analyzer and a Cochlear Implant System" to Kinuko Masaki et al., client docket number 3021-0321-WO, which application is to be filed as a PCT application on the same day as the present application. The 3021-0321-WO application is incorporated herein by reference in its entirety.

In some examples, stimulation management facility 102 may be further configured to prevent the cochlear implant system from applying an electrical stimulus for more than a predetermined amount of time. For example, stimulation management facility 102 may limit the duration of the electrical stimulus to an amount of time that is less than the time required for sound saturation. This amount of time may be 200 ms or any other suitable amount of time as may serve a particular implementation.

Detection facility 104 may be configured to determine that a change in acoustic immittance that occurs as an electrical stimulus is being applied to a patient by a cochlear implant system is likely representative of a rise time phase associated with an occurrence of a stapedius reflex within the patient. To facilitate an understanding of the term "rise time phase," an exemplary stapedius reflex will be described in connection with FIG. 2.

Figure 2:
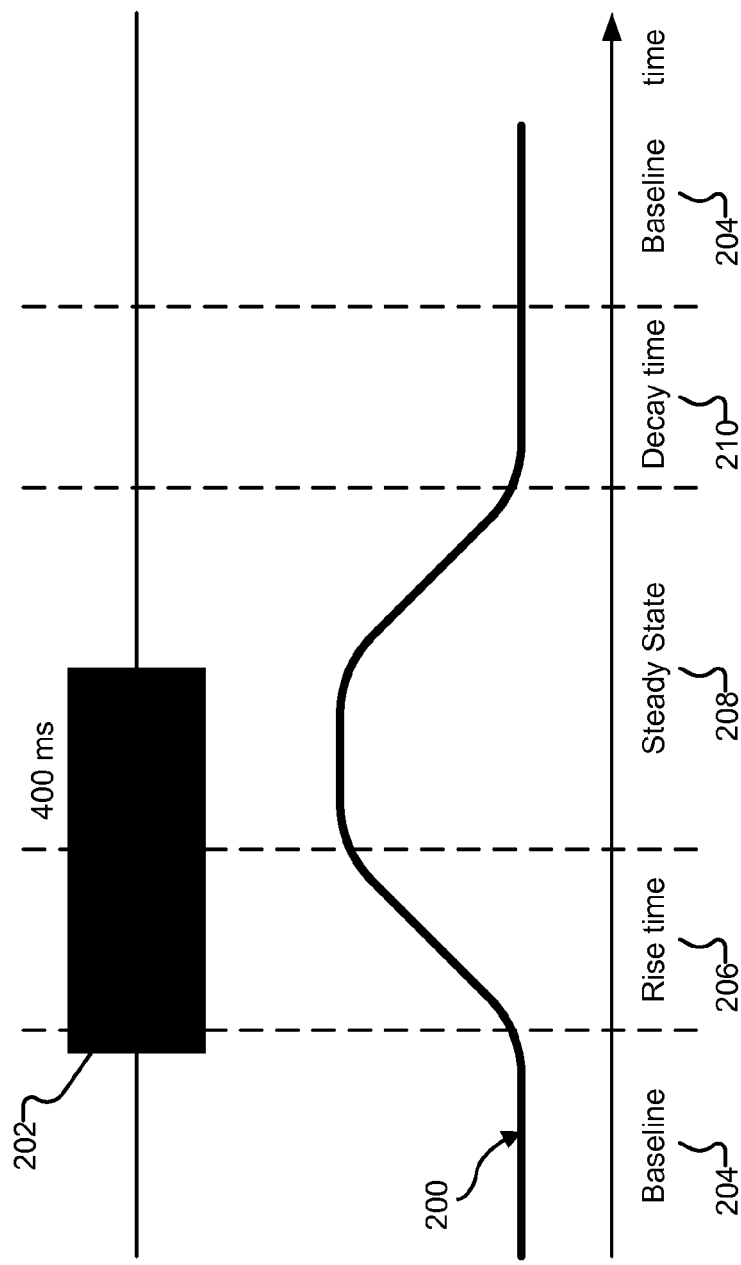
FIG. 2 illustrates an exemplary change in acoustic immittance that may be detected in response to an application of an electrical stimulus to an auditory pathway of a cochlear implant patient according to principles described herein.

FIG. 2 illustrates an exemplary acoustic immittance curve 200 that represents various acoustic immittance values that may be detected by a middle ear analyzer as an electrical stimulus 202 is applied to an auditory pathway of a cochlear implant patient. Electrical stimulus 202 may have a current level large enough to elicit a stapedius reflex and may be of any suitable shape and duration as may serve a particular implementation. For example, in the particular example of FIG. 2, electrical stimulus 202 has a duration of 400 ms.

As shown by acoustic immittance curve 200, prior to application of electrical stimulus 202, the detected acoustic immittance is in a baseline phase 204, which indicates that the stapedius reflex has not yet occurred. However, immediately after commencement of the electrical stimulus 202, the detected acoustic immittance begins to increase in amplitude, as represented by rise time phase 206. After a period of time, the detected acoustic immittance remains constant, as represented by steady state phase 208. Upon completion of the electrical stimulus 202, the detected acoustic immittance decreases in amplitude, as represented by decay time phase 210, and returns to baseline phase 204.

As mentioned, for some cochlear implant patients, application of electrical stimulus 202 does not elicit a stapedius reflex such as that shown in FIG. 2. For these patients, the detected acoustic immittance may remain in the baseline phase 204 throughout the entire application of electrical stimulus 202. Additional attempts to elicit a stapedius reflex in these types of patients by increasing the current level of electrical stimulus 202 may be equally unfruitful.

Conventional stapedius reflex measurement techniques involve applying electrical stimulus 202 for a period of time that is long enough to elicit a full stapedius reflex (i.e., long enough to elicit rise time phase 206, steady-state phase 208, and decay time phase 210). Unfortunately, this period of time is typically longer than that required for sound saturation to occur. For example, electrical stimulus 202 may be applied for 400 ms, as shown in FIG. 2, in order to elicit a full stapedius reflex. However, sound saturation associated with electrical stimulus 202 may occur after electrical stimulus 202 has been applied for approximately 200 ms. Hence, if the current level of electrical stimulus 202 is greater than the M level of the patient, the patient may perceive an uncomfortably loud sound and/or incur damage to the ear as a result of the application of electrical stimulus 202. However, as will be described below, electrical stimulus 202 may be limited in time (e.g., to approximately 200 ms or less) and ceased prior to the onset of sound saturation (e.g., as soon as a detected change in acoustic immittance indicates that rise time state 206 is occurring), thereby reducing the loudness level perceived by the patient and avoiding potential patient discomfort, pain, and/or damage.

Returning to FIG. 1, detection facility 104 may determine that a change in acoustic immittance is likely representative of a rise time phase associated with an occurrence of a stapedius reflex in any suitable manner. For example, detection facility 104 may determine that a change in acoustic immittance is likely representative of a rise time phase by determining that the change in acoustic immittance is equal to or above a predetermined threshold. Additionally or alternatively, detection facility 104 may determine that a change in acoustic immittance is likely representative of a rise time phase by detecting a change in slope of acoustic immittance curve 200.

To illustrate, a middle ear analyzer may record data representative of a plurality of acoustic immittance values that are detected as an electrical stimulus is being applied to the patient. The data may be provided (e.g., transmitted) in real time to detection facility 104, which may receive and analyze the data to determine that a change in the acoustic immittance over time is equal to or above a predetermined threshold and/or that a slope of an acoustic immittance curve representative of the acoustic immittance has changed above a predetermined threshold.

In response to a determination by detection facility 104 that a change in acoustic immittance is likely representative of a rise time phase associated with an occurrence of a stapedius reflex, stimulation management facility 102 may direct the cochlear implant system to cease applying the electrical stimulus. This may be performed in any suitable manner. For example, stimulation management facility 102 may direct the cochlear implant system to cease applying the electrical stimulus before an occurrence of a steady state phase associated with the stapedius reflex (e.g., steady state phase 208).

A clinician may determine whether a change in acoustic immittance is representative of an actual rise time phase associated with a stapedius reflex in any suitable manner. For example, the clinician may direct system 100 to repeat the measurement process one or more times with the same current level to determine whether the same rise time phase is detected during each measurement. If it is, the clinician may designate the current level as a stapedius reflex threshold (i.e., a current level that elicits an occurrence of a stapedius reflex). Additionally or alternatively, the clinician may direct system 100 to apply the electrical stimulus for a longer duration so that a full stapedius reflex may occur.

However, if the same rise time phase cannot be consistently detected, the clinician may determine that the change in acoustic immittance is representative of something other than stapedius reflex (e.g., a noise artifact). In this case, the clinician may decide to increase the current level and again attempt to generate a stapedius reflex or take some other action.

Storage facility 106 may be configured to maintain control data 108 generated and/or used by stimulation management facility 102 and stapedius reflex data 110 generated and/or used by detection facility 104. It will be recognized that storage facility 106 may maintain additional or alternative data as may serve a particular implementation.

Figure 3:
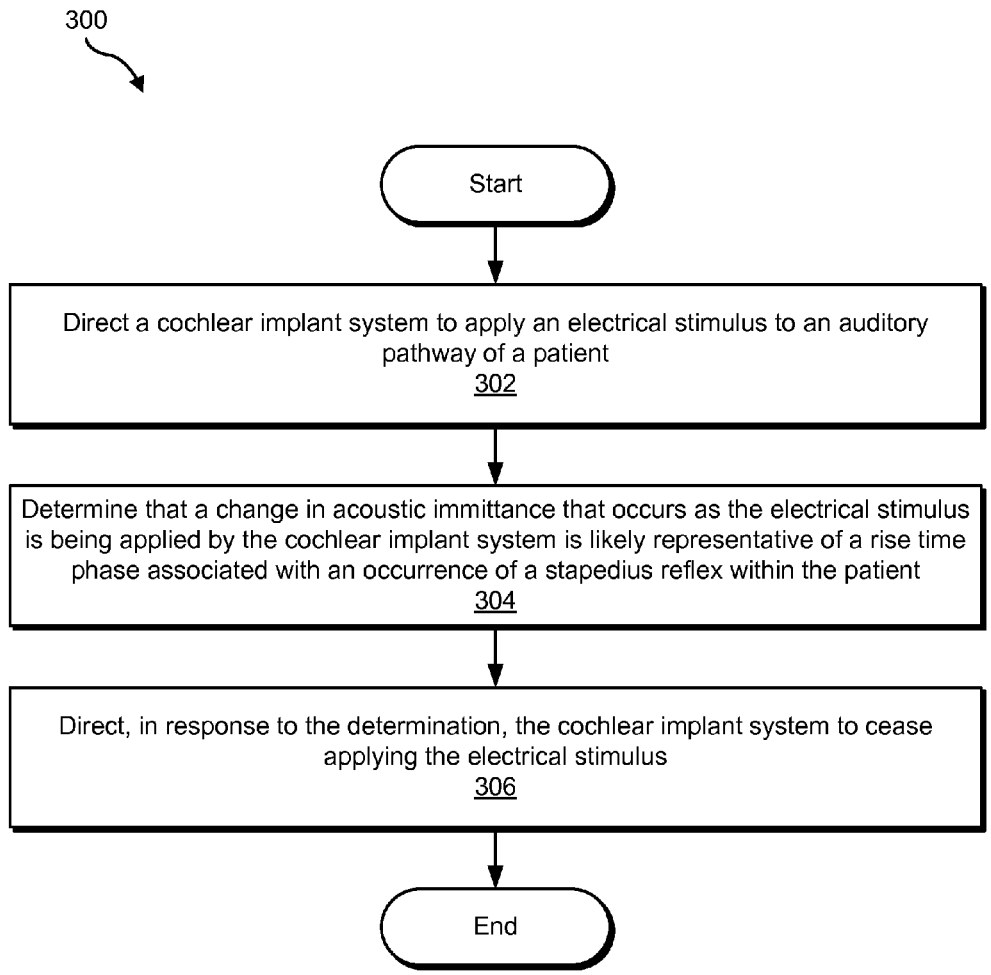
FIG. 3 illustrates an exemplary stapedius reflex measurement safety method according to principles described herein.

FIG. 3 illustrates an exemplary stapedius reflex measurement safety method 300. While FIG. 3 illustrates exemplary steps according to one embodiment, other embodiments may omit, add to, reorder, and/or modify any of the steps shown in FIG. 3. One or more of the steps shown in FIG. 3 may be performed by system 100 and/or any implementation thereof.

In step 302, a stapedius reflex measurement safety system directs a cochlear implant system to apply an electrical stimulus to an auditory pathway of a patient. Step 302 may be performed in any of the ways described herein.

In step 304, the stapedius reflex measurement safety system determines that a change in acoustic immittance that occurs as the electrical stimulus is being applied by the cochlear implant system is likely representative of a rise time phase associated with an occurrence of a stapedius reflex within the patient. Step 304 may be performed in any of the ways described herein.

In step 306, the stapedius reflex measurement safety system directs, in response to the determination, the cochlear implant system to cease applying the electrical stimulus. Step 306 may be performed in any of the ways described herein.

Figure 4:
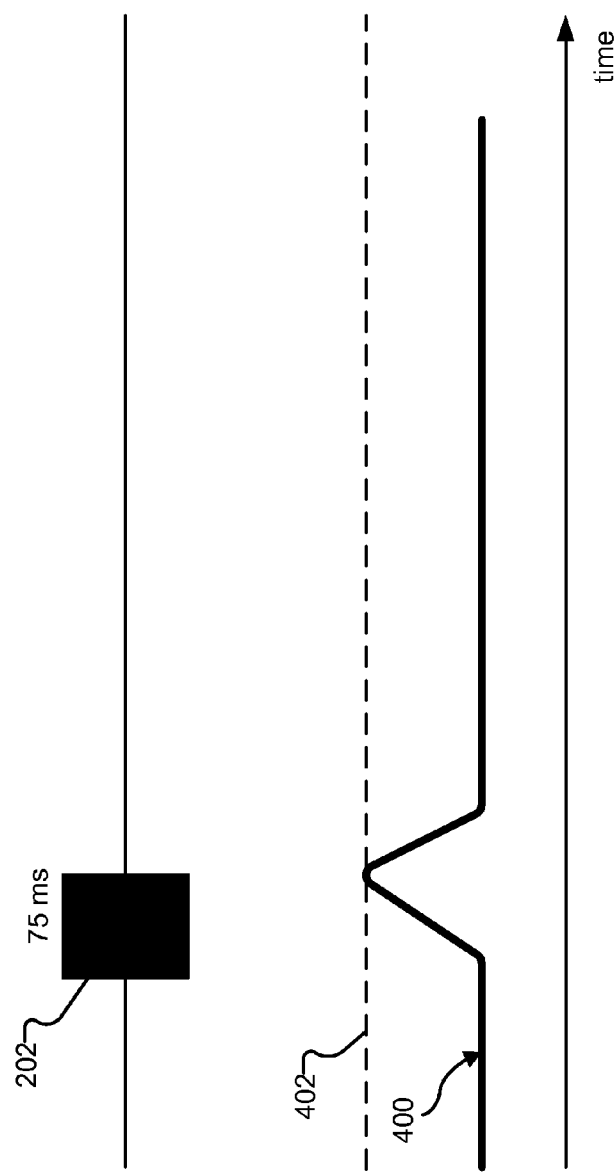
FIG. 4 illustrates an exemplary change in acoustic immittance that may be detected (e.g., by a middle ear analyzer) in response to an application of a relatively short duration electrical stimulus according to principles described herein.

An example of the systems and methods described herein will now be provided in connection with FIG. 4. FIG. 4 illustrates an exemplary acoustic immittance curve 400 that represents various acoustic immittance values that may be detected by a middle ear analyzer as the same electrical stimulus 202 shown in FIG. 2 is applied to an auditory pathway of a cochlear implant patient. However, in the example of FIG. 4, system 100 directs the cochlear implant system to cease applying electrical stimulus 202 after system 100 detects that the acoustic immittance represented by acoustic immittance curve 400 has reached a predetermined threshold 402, which indicates that a rise time phase associated with a stapedius reflex has likely occurred. In the example of FIG. 4, this occurs after electrical stimulus 202 has been applied for 75 ms. Hence, the patient is only subjected to 75 ms of electrical stimulus 202 instead of the full 400 ms shown in FIG. 2. The reduced stimulation time is not long enough for sound saturation to occur, thereby ensuring patient safety.

As mentioned, the measurement shown in FIG. 4 may be repeated one or more times (e.g., ten times) to verify that the change in acoustic immittance is representative of a rise time phase associated with an actual stapedius reflex. If system 100 and/or clinician determines that the detected change in acoustic immittance is associated with an actual stapedius reflex, the clinician may determine that the change in acoustic immittance is indeed representative of an occurrence of a stapedius reflex. The current level of the electrical stimulus used to elicit the stapedius reflex may then be used as a starting point for determining an M level associated with the patient. In some examples, system 100 may present data representative of this current level within a GUI or in any other manner as may serve a particular implementation.

Figure 5:
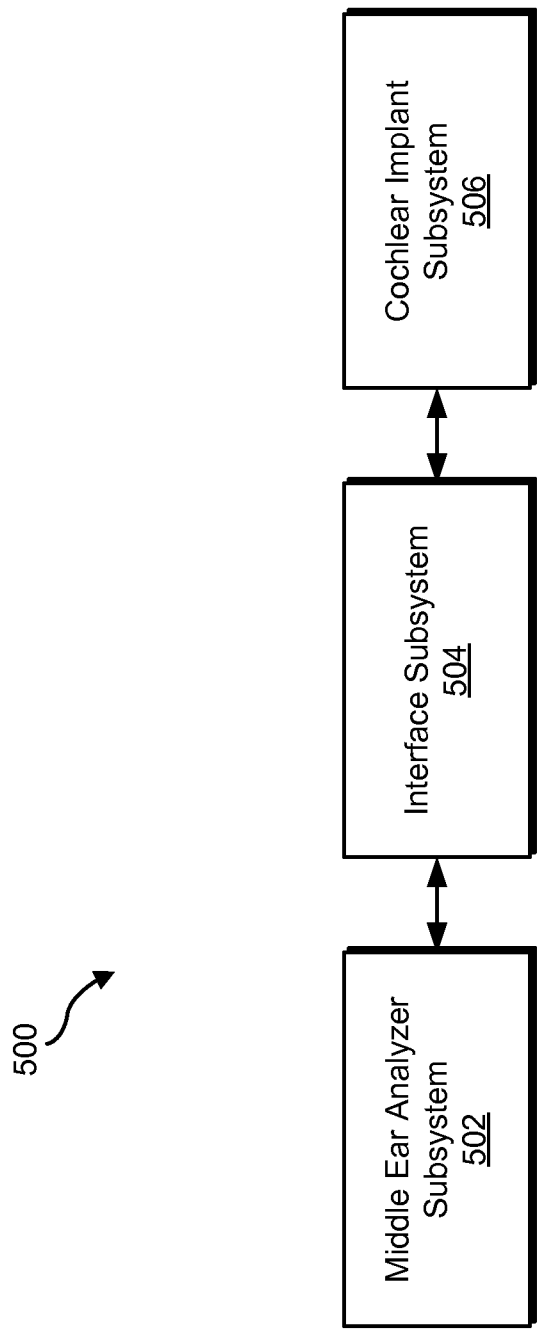
FIGS. 5-7 illustrate exemplary implementations of the system of FIG. 1 according to principles described herein.

FIG. 5 illustrates an exemplary implementation 500 of system 100. As shown, implementation 500 may include a middle ear analyzer subsystem 502, an interface subsystem 504, and a cochlear implant subsystem 506 communicatively coupled to one another. Facilities 102-106 may each be implemented by one or more of subsystems 502-506.

As described above, middle ear analyzer subsystem 502 may generate and transmit an acoustic signal to interface subsystem 504. Interface subsystem 504 may receive the acoustic signal transmitted by middle ear analyzer subsystem 502, detect a sound level of the acoustic signal, identify a current level associated with the detected sound level, and direct a cochlear implant subsystem to apply an electrical stimulus having the identified current level to one or more stimulation sites within a patient.

Middle ear analyzer subsystem 502 may detect a change in acoustic immittance that occurs in response to the application of the electrical stimulus by the cochlear implant subsystem. Interface subsystem 504 may receive data representative of a detected change in acoustic immittance from middle ear analyzer subsystem 502, determine that the change in acoustic immittance is equal to or above a predetermined threshold, and direct, in response to the determination, cochlear implant subsystem 506 to cease applying the electrical stimulus.

To facilitate identification of a current level associated with the detected sound level, interface subsystem 504 may maintain mapping data representative of an association between a plurality of sound levels and a plurality of current levels. Mapping data may be maintained in the form of a look-up table, in a database, and/or in any other manner as may serve a particular implementation.

To illustrate, Table 1 illustrates mapping data representative of an exemplary association between a plurality of sound levels and a plurality of current levels that may be maintained by interface subsystem 504.

TABLE 1

| Sound Level (dB SPL) | Current Level (CU) |
|---|---|
| 80 | 110 |
| 85 | 120 |

TABLE 1-continued

| Sound Level (dB SPL) | Current Level (CU) |
|---|---|
| 90 | 130 |
| 95 | 140 |
| 100 | 150 |

As shown in Table 1, the mapping data indicates that a sound level of 80 dB SPL is mapped to a current level of 110 clinical units ("CU"), a sound level of 85 dB SPL is mapped to a current level of 120 CU, a sound level of 90 dB SPL is mapped to a current level of 130 CU, a sound level of 95 dB SPL is mapped to a current level of 140 CU, and a sound level of 100 dB SPL is mapped to a current level of 150 CU. Interface subsystem 504 may use the mapping data illustrated in Table 1 to identify a current level that is associated with a sound level of a particular acoustic signal detected by interface subsystem 504. It will be recognized that the mapping associations between current level and sound level illustrated in Table 1 are merely illustrative of the many different mapping associations that may be utilized in accordance with the systems and methods described herein.

In some examples, interface subsystem 504 may additionally be configured to detect a frequency of an acoustic signal provided by middle ear analyzer subsystem 502 and identify one or more electrodes to which the electrical stimulus is to be applied based on the detected frequency. For example, Table 2 illustrates additional mapping data representative of an exemplary association between a plurality of frequencies and a plurality of electrodes (e.g., a plurality of electrodes included on a lead configured to be implanted within a cochlea of a patient) that may be maintained by interface subsystem 504.

TABLE 2

| Frequency (kHz) | Electrode Numbers |
|---|---|
| 1 | 1-4 |
| 2 | 5-8 |
| 3 | 9-12 |
| 4 | 13-16 |

As shown in Table 2, the additional mapping data indicates that a frequency of 1 kHz is mapped to electrodes 1 through 4, a frequency of 2 kHz is mapped to electrodes 5 through 8, a frequency of 3 kHz is mapped to electrodes 9 through 12, and a frequency of 4 kHz is mapped to electrodes 13 through 16. Interface subsystem 504 may use the mapping data illustrated in Table 2 to identify one or more electrodes that are associated with a frequency of a particular acoustic signal provided by middle ear analyzer 502. It will be recognized that the mapping associations between frequency and electrode numbers illustrated in Table 2 are merely illustrative of the many different mapping associations that may be utilized in accordance with the systems and methods described herein.

Cochlear implant subsystem 506 (also referred to herein as a "cochlear implant system") may be configured to generate and apply electrical stimuli to a patient. For example, a sound processor located external to the patient may use control data provided by interface subsystem 504 to generate one or more stimulation parameters configured to direct a cochlear implant implanted within the patient to generate and apply the electrical stimulation.

Figure 6:
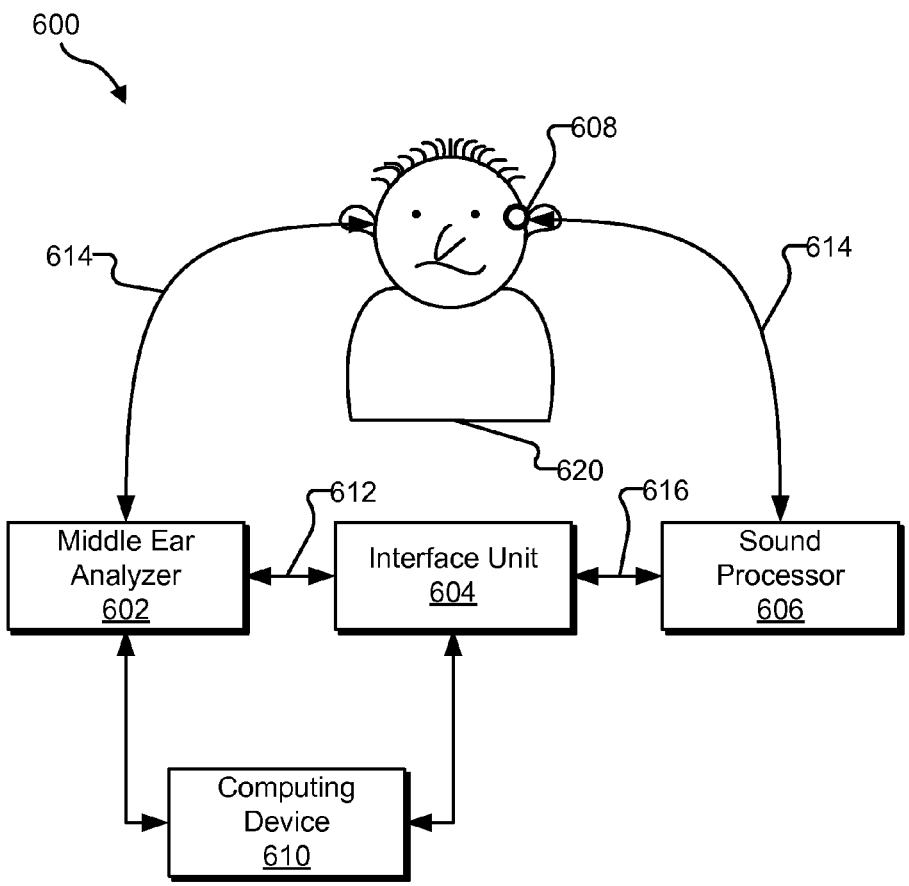

FIG. 6 illustrates an exemplary implementation 600 of middle ear analyzer subsystem 502, interface subsystem 504, and cochlear implant subsystem 506. As shown, implementation 600 may include a middle ear analyzer 602, an interface unit 604, a sound processor 606, a cochlear implant 608, and a computing device 610. Implementation 600 may further include a stimulation probe 612 configured to communicatively couple middle ear analyzer 602 and interface unit 604 and a detection probe 614 configured to be coupled to middle ear analyzer 602 and detect a change in immittance that occurs as a result of electrical stimulation applied by way of one or more electrodes (not shown) communicatively coupled to cochlear implant 608.

Middle ear analyzer subsystem 502, interface subsystem 504, and cochlear implant subsystem 506 may each be implemented by one or more components illustrated in FIG. 6. For example, middle ear analyzer subsystem 502 may be implemented by a middle ear analyzer 602, stimulation probe 612, detection probe 614, and computing device 610. Interface subsystem 504 may be implemented by interface unit 604 and computing device 610. Cochlear implant subsystem 506 may be implemented by sound processor 606 and cochlear implant 608.

Each of the components shown in FIG. 6 will now be described in more detail. Middle ear analyzer 602 may include any suitable middle ear analyzer (e.g. an off-the-shelf middle ear analyzer) configured to perform one or more of the middle ear analyzer operations described herein. For example, middle ear analyzer 602 may be configured to operate in a contralateral stimulation mode in which middle ear analyzer 602 is configured to generate and apply acoustic stimulation (i.e., one or more acoustic signals) by way of stimulation probe 612 and record a resulting change in immittance using detection probe 614.

Interface unit 604 may be configured to perform one or more interface operations as described herein. For example, interface unit 604 may include any combination of signal receivers, signal transmitters, processors, and/or computing devices configured to receive an acoustic signal transmitted by a middle ear analyzer 602 by way of stimulation probe 612, detect a sound level of the acoustic signal, and transmit control data representative of a current level associated with the sound level to sound processor 606.

Interface unit 604 may be coupled directly to middle ear analyzer 602 by way of stimulation probe 612. Interface unit 604 may also be coupled to sound processor 606 by way of communication channel 616, which may include any suitable wired and/or wireless communication channel as may serve a particular implementation.

Sound processor 606 may include any type of sound processor used in a cochlear implant system as may serve a particular implementation. For example, sound processor 606 may include a behind-the-ear ("BTE") sound processing unit, a portable speech processor ("PSP"), and/or a body-worn processor.

Cochlear implant 608 may include any suitable auditory prosthesis configured to be at least partially implanted within a patient as may serve a particular implementation. For example, cochlear implant 608 may include an implantable cochlear stimulator, a brainstem implant and/or any other type of auditory prosthesis. In some examples, cochlear implant 608 may be communicatively coupled to a lead having a plurality of electrodes (e.g., sixteen electrodes) disposed thereon. The lead may be configured to be implanted within the patient such that the electrodes are in communication with stimulation sites (e.g., locations within the cochlea) within the patient. As used herein, the term "in communication with"

refers to an electrode being adjacent to, in the general vicinity of, in close proximity to, directly next to, or directly on a stimulation site.

Sound processor 606 and cochlear implant 608 may communicate by way of communication channel 614. Communication channel 614 may be wired or wireless as may serve a particular implementation.

Computing device 610 may include any combination of computing devices (e.g., personal computers, mobile computing devices (e.g., mobile phones, tablet computers, laptop computers, etc.), fitting stations, etc.). As shown, computing device 610 may be communicatively coupled (e.g., with one or more cables) to both the middle ear analyzer 602 and the interface unit 604. As such, computing device 610 may be configured to perform one or more of the operations associated with the middle ear analyzer 602 and the interface unit 604. For example, computing device 610 may generate and present one or more GUIs by way of a display device (e.g., a display screen included within computing device 610 and/or communicatively coupled to computing device 610) associated with an operation of middle ear analyzer 602 and/or interface unit 604.

Additionally or alternatively, computing device 610 may be configured to store, maintain, process, and/or otherwise maintain the mapping data utilized by interface subsystem 504. For example, computing device 610 may be configured to maintain a database comprising the mapping data and identify current levels and/or electrodes associated with an acoustic signal received by interface unit 604.

In some alternative examples, separate computing devices may be associated with middle ear analyzer 602 and interface unit 604. For example, a first computing device may be communicatively coupled to middle ear analyzer 602 and configured to perform one or more operations associated with middle ear analyzer 602 and a second computing device may be communicatively coupled to interface unit 604 and configured to perform one or more operations associated with interface unit 604.

In an exemplary configuration, detection probe 614 is placed within one of the ears of a patient 620. In some examples, as shown in FIG. 6, the ear in which detection probe 614 is placed is contralateral to the ear associated with cochlear implant 608. Alternatively, detection probe 614 may be placed within the same ear associated with cochlear implant 608.

Figure 7:
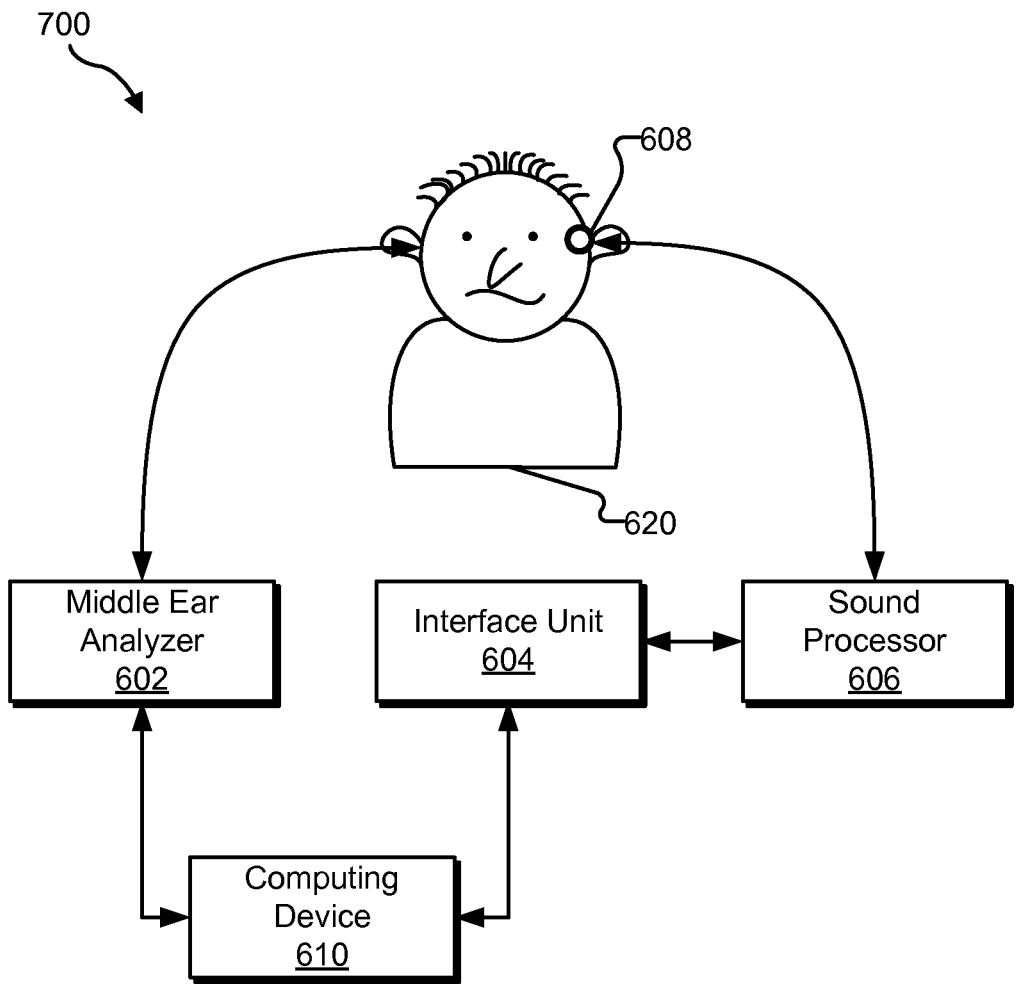

FIG. 7 illustrates another exemplary implementation 700 of middle ear analyzer subsystem 502, interface subsystem 504, and cochlear implant subsystem 506. Implementation 700 is similar to implementation 600, except that middle ear analyzer 602 does not generate and provide an acoustic signal to interface unit 604. Rather, interface unit 604 is configured to independently direct sound processor 606 and cochlear implant 608 to generate electrical stimuli. Interface unit 604 may still communicate with middle ear analyzer 602 by way of computing device 610.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a CD-ROM, DVD, any other optical medium, a RAM, a PROM, an EPROM, a FLASH-EEPROM, any other memory chip or cartridge, or any other tangible medium from which a computer can read.

Figure 8:
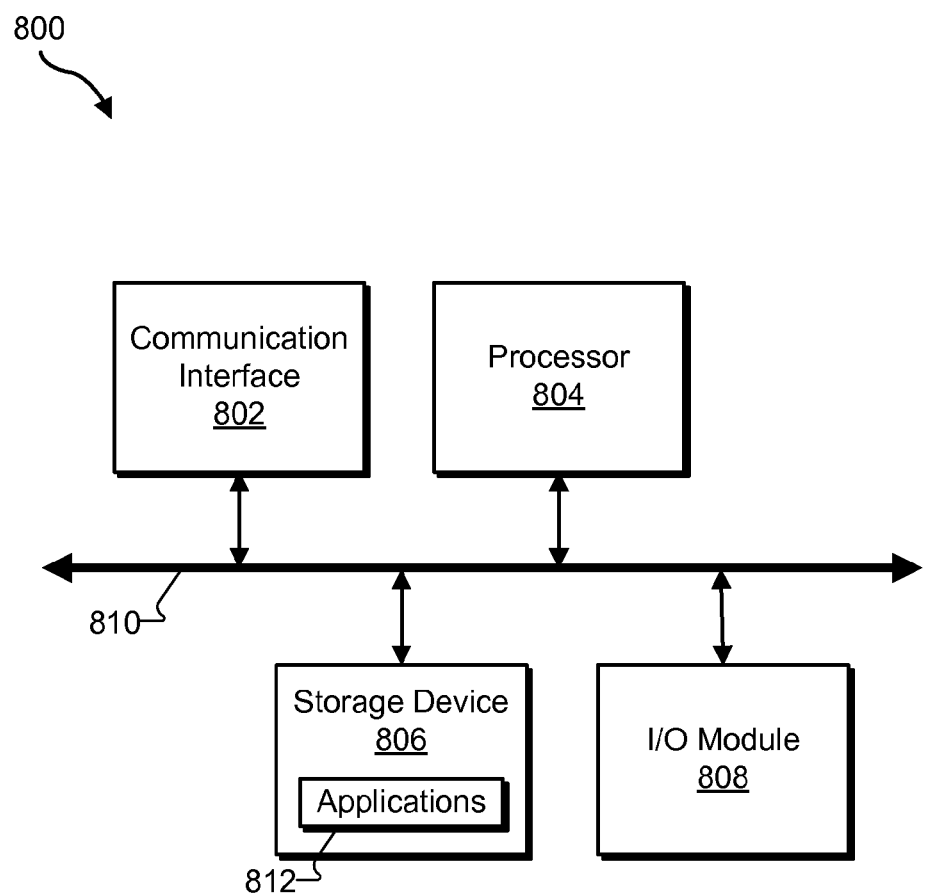
FIG. 8 illustrates an exemplary computing device according to principles described herein.

FIG. 8 illustrates an exemplary computing device 800 that may be configured to perform one or more of the processes described herein. As shown in FIG. 8, computing device 800 may include a communication interface 802, a processor 804, a storage device 806, and an input/output ("I/O") module 808 communicatively connected via a communication infrastructure 810. While an exemplary computing device 800 is shown in FIG. 8, the components illustrated in FIG. 8 are not intended to be limiting. Additional or alternative components may be used in other embodiments. Components of computing device 800 shown in FIG. 8 will now be described in additional detail.

Communication interface 802 may be configured to communicate with one or more computing devices. Examples of communication interface 802 include, without limitation, a wired network interface (such as a network interface card), a wireless network interface (such as a wireless network interface card), a modem, an audio/video connection, and any other suitable interface.

Processor 804 generally represents any type or form of processing unit capable of processing data or interpreting, executing, and/or directing execution of one or more of the instructions, processes, and/or operations described herein. Processor 804 may direct execution of operations in accordance with one or more applications 812 or other computer-executable instructions such as may be stored in storage device 806 or another computer-readable medium.

Storage device 806 may include one or more data storage media, devices, or configurations and may employ any type, form, and combination of data storage media and/or device. For example, storage device 806 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 806. For example, data representative of one or more executable applications 812 configured to direct processor 804 to perform any of the operations described herein may be stored within storage device 806. In some examples, data may be arranged in one or more databases residing within storage device 806.

I/O module 808 may be configured to receive user input and provide user output and may include any hardware, firmware, software, or combination thereof supportive of input and output capabilities. For example, I/O module 808 may include hardware and/or software for capturing user input, including, but not limited to, a keyboard or keypad, a touch screen component (e.g., touch screen display), a receiver (e.g., an RF or infrared receiver), and/or one or more input buttons.

I/O module 808 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 808 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 800. For example, one or more applications 812 residing within storage device 806 may be configured to direct processor 804 to perform one or more processes or functions associated with any of the facilities and/or subsystems described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
   at least one computing device configured to:
   direct a cochlear implant system to apply an electrical stimulus to an auditory pathway of a patient;
   determine that a change in acoustic immittance that occurs as the electrical stimulus is being applied by the cochlear implant system is likely representative of a rise time phase associated with an occurrence of a stapedius reflex within the patient by determining that the change in acoustic immittance is equal to or above a predetermined threshold; and
   direct, in response to the determination, the cochlear implant system to cease applying the electrical stimulus before an occurrence of a steady state phase associated with the stapedius reflex.

2. The system of claim 1, wherein the electrical stimulus has a predetermined current level, and wherein the at least one computing device is further configured to:
   direct the cochlear implant system to apply an additional electrical stimulus having the predetermined current level to the auditory pathway of the patient;
   determine that a change in acoustic immittance that occurs as the additional electrical stimulus is being applied by the cochlear implant system is again likely representative of a rise time phase associated with another occurrence of the stapedius reflex within the patient;
   direct, in response to the determination that the change in acoustic immittance that occurs as the additional electrical stimulus is being applied by the cochlear implant system is likely representative of the rise time phase, the cochlear implant system to cease applying the electrical stimulus, and
   designate the predetermined current level as a starting point for determining a most comfortable current level associated with the patient.

3. The system of claim 1, wherein the at least one computing device is further configured to designate a current level of the electrical stimulus as a starting point for determining a most comfortable current level associated with the patient.

4. The system of claim 3, wherein the at least one computing device is further configured to present, within a graphical user interface, data representative of the current level.

5. The system of claim 1, wherein the at least one computing device is configured to direct the cochlear implant system to apply the electrical stimulus by transmitting control data representative of a current level to be used for the electrical stimulus to a sound processor included in the cochlear implant system.

6. The system of claim 1, wherein the at least one computing device is configured to direct the cochlear implant system to apply the electrical stimulus by:
   receiving an acoustic signal transmitted by a middle ear analyzer;
   detecting a sound level of the acoustic signal;
   identifying a current level associated with the detected sound level; and
   directing the cochlear implant system to apply a stimulation pulse having the identified current level.

7. The system of claim 1, wherein the at least one computing device is further configured to determine that the change in acoustic immittance is likely representative of the rise time phase by detecting that a slope of an acoustic immittance curve representative of the acoustic immittance has changed above a predetermined threshold.

8. The system of claim 1, wherein the at least one computing device is further configured to prevent the cochlear implant system from applying the electrical stimulus for more than a predetermined amount of time.

9. A method comprising:
   directing, by a stapedius reflex measurement safety system, a cochlear implant system to apply an electrical stimulus to an auditory pathway of a patient;
   determining, by the stapedius reflex measurement safety system, that a change in acoustic immittance that occurs as the electrical stimulus is being applied by the cochlear implant system is likely representative of a rise time phase associated with an occurrence of a stapedius reflex within the patient by determining that the change in acoustic immittance is equal to or above a predetermined threshold; and
   directing, by the stapedius reflex measurement safety system in response to the determining, the cochlear implant system to cease applying the electrical stimulus before an occurrence of a steady state phase associated with the stapedius reflex.

10. The method of claim 9, wherein the directing of the cochlear implant system to cease applying the electrical stimulus comprises preventing the electrical stimulus from being applied for more than a predetermined amount of time.

11. The method of claim 9, embodied as computer-executable instructions on at least one non-transitory computer-readable medium.

12. The method of claim 9, wherein the electrical stimulus has a predetermined current level, and wherein the method further comprises:
   directing, by the stapedius reflex measurement safety system, the cochlear implant system to apply an additional electrical stimulus having the predetermined current level to the auditory pathway of the patient;
   determining, by the stapedius reflex measurement safety system, that a change in acoustic immittance that occurs as the additional electrical stimulus is being applied by the cochlear implant system is again likely representative of a rise time phase associated with another occurrence of the stapedius reflex within the patient;

directing, by the stapedius reflex measurement safety system in response to the determination that the change in acoustic immittance that occurs as the additional electrical stimulus is being applied by the cochlear implant system is likely representative of the rise time phase, the cochlear implant system to cease applying the electrical stimulus; and designating, by the stapedius reflex measurement safety system, the predetermined current level as a starting point for determining a most comfortable current level associated with the patient.

13. The method of claim 9, further comprising designating, by the stapedius reflex measurement safety system, a current level of the electrical stimulus as a starting point for determining a most comfortable current level associated with the patient.

14. The method of claim 13, further comprising presenting, by the stapedius reflex measurement safety system within a graphical user interface, data representative of the current level.

15. The method of claim 9, further comprising directing, by the stapedius reflex measurement safety system, the cochlear implant system to apply the electrical stimulus by transmitting control data representative of a current level to be used for the electrical stimulus to a sound processor included in the cochlear implant system.

16. The method of claim 9, wherein the directing of the cochlear implant system to apply the electrical stimulus comprises:

receiving an acoustic signal transmitted by a middle ear analyzer;

detecting a sound level of the acoustic signal;

identifying a current level associated with the detected sound level; and directing the cochlear implant system to apply a stimulation pulse having the identified current level.

17. The method of claim 9, wherein the determining that the change in acoustic immittance is likely representative of the rise time phase further comprises detecting that a slope of an acoustic immittance curve representative of the acoustic immittance has changed above a predetermined threshold.

* * * * *